(12) United States Patent
Beuchat

(10) Patent No.: US 11,253,666 B2
(45) Date of Patent: Feb. 22, 2022

(54) MASKS, SYSTEMS, AND METHODS FOR ASSISTING RESPIRATION INCLUDING SCATTERING CHAMBER

(71) Applicants: Nihon Kohden America, Inc., Irvine, CA (US); Nihon Kohden Corporation, Tokyo (JP)

(72) Inventor: Charles Edward Beuchat, Irvine, CA (US)

(73) Assignees: Nihon Kohden America, Inc., Irvine, CA (US); Nihon Kohden Corporation, Tokyo (JP)

( * ) Notice: Subject to any disclaimer, the term of this patent is extended or adjusted under 35 U.S.C. 154(b) by 460 days.

(21) Appl. No.: 16/319,795

(22) PCT Filed: Jul. 18, 2017

(86) PCT No.: PCT/US2017/042582
§ 371 (c)(1),
(2) Date: Jan. 22, 2019

(87) PCT Pub. No.: WO2018/017565
PCT Pub. Date: Jan. 25, 2018

(65) Prior Publication Data
US 2019/0275277 A1 Sep. 12, 2019

Related U.S. Application Data

(60) Provisional application No. 62/365,730, filed on Jul. 22, 2016.

(51) Int. Cl.
*A61M 16/06* (2006.01)
*A61M 16/08* (2006.01)
(Continued)

(52) U.S. Cl.
CPC ........ *A61M 16/06* (2013.01); *A61M 16/0816* (2013.01); *A61B 5/08* (2013.01);
(Continued)

(58) Field of Classification Search
CPC ..... A61B 5/08; A61M 16/06; A61M 16/0816; A61M 16/085; A61M 2016/102;
(Continued)

(56) References Cited

U.S. PATENT DOCUMENTS

| | | | | |
|---|---|---|---|---|
| 1,926,027 A | * | 9/1933 | Biggs | A62B 18/00 128/205.25 |
| 2,174,523 A | | 10/1939 | Manson | |

(Continued)

FOREIGN PATENT DOCUMENTS

| | | |
|---|---|---|
| CN | 103974735 A | 8/2014 |
| CN | 104548304 A | 4/2015 |

(Continued)

OTHER PUBLICATIONS

International Search Report and Written Opinion for PCT Application No. PCT/US2017/042582, dated Oct. 6, 2017.
(Continued)

*Primary Examiner* — Annette Dixon
(74) *Attorney, Agent, or Firm* — Dorsey & Whitney LLP

(57) ABSTRACT

A mask configured to assist the respiration of a patient with a gas inlet port positioned to connect a gas supply to the mask and direct gas flow towards a patient's skin; a scattering chamber with an inlet port and a plurality of outlet ports, the scattering chamber inlet port fluidly connected to the gas inlet port, and the plurality of outlet ports positioned to scatter the gas flow away from the patient's skin and towards the interior surface of the mask and a region between the patient's skin and the interior surface of the mask; and an outgas collector assembly connected adjacent (Continued)

the scattering chamber and positioned to collect an outgas emission expelled from the patient and eject the outgas emission from the mask.

24 Claims, 15 Drawing Sheets

(51) Int. Cl.
*A61M 16/10* (2006.01)
*A61B 5/08* (2006.01)

(52) U.S. Cl.
CPC ..... *A61M 16/085* (2014.02); *A61M 2016/102* (2013.01); *A61M 2202/0208* (2013.01); *A61M 2202/0266* (2013.01); *A61M 2202/0283* (2013.01); *A61M 2206/10* (2013.01); *A61M 2206/20* (2013.01); *A61M 2210/0618* (2013.01); *A61M 2210/0625* (2013.01); *A61M 2230/43* (2013.01)

(58) Field of Classification Search
CPC .. A61M 2202/0208; A61M 2202/0266; A61M 2202/0283; A61M 2206/10; A61M 2206/20; A61M 2210/0618; A61M 2210/0625; A61M 2230/43
See application file for complete search history.

(56) References Cited

U.S. PATENT DOCUMENTS

| | | | |
|---|---|---|---|
| 2,313,999 A | | 3/1943 | Kreishelman |
| 2,675,803 A | | 4/1954 | Kaslow |
| 3,682,171 A | | 8/1972 | Dali et al. |
| 3,889,671 A | | 6/1975 | Baker |
| 4,201,205 A | | 5/1980 | Bartholomew |
| 4,207,888 A | | 6/1980 | Ghormley |
| 4,216,769 A | | 8/1980 | Grimes |
| 4,258,710 A | * | 3/1981 | Reber .................. A62B 18/003 128/200.27 |
| 4,266,540 A | | 5/1981 | Panzik et al. |
| 4,454,880 A | | 6/1984 | Muto et al. |
| 4,739,753 A | * | 4/1988 | Brehm .............. A61M 16/0627 128/200.24 |
| 4,832,042 A | * | 5/1989 | Poppendiek ...... A61M 16/0627 600/543 |
| 4,848,333 A | * | 7/1989 | Waite .................... A61M 16/12 128/205.11 |
| 4,949,714 A | * | 8/1990 | Orr ........................ A61G 10/04 128/200.24 |
| 5,335,653 A | * | 8/1994 | Blomqvist ............. A61B 5/083 128/200.24 |
| 5,832,919 A | * | 11/1998 | Kano ..................... A62B 31/00 128/205.26 |
| 6,247,470 B1 | * | 6/2001 | Ketchedjian ...... A61M 16/0666 128/200.28 |
| 6,561,190 B1 | | 5/2003 | Kwok |
| 6,595,207 B1 | | 7/2003 | McDonald et al. |
| 6,871,651 B2 | * | 3/2005 | Lanier .................... A61B 46/00 128/849 |
| 7,040,319 B1 | | 5/2006 | Kelly et al. |
| 8,707,950 B1 | | 4/2014 | Rubin |
| 2001/0042547 A1 | | 11/2001 | McDonald et al. |
| 2003/0168063 A1 | | 9/2003 | Gambone et al. |
| 2005/0257794 A1 | | 11/2005 | Aylsworth et al. |
| 2006/0196510 A1 | | 9/2006 | McDonald et al. |
| 2007/0175473 A1 | | 8/2007 | Lewis et al. |
| 2008/0060649 A1 | | 3/2008 | Veliss et al. |
| 2008/0092898 A1 | | 4/2008 | Schneider et al. |
| 2008/0196715 A1 | | 8/2008 | Yamamori |
| 2008/0319334 A1 | | 12/2008 | Yamamori |
| 2011/0015534 A1 | | 1/2011 | Yamamori |
| 2011/0041855 A1 | | 2/2011 | Gunaratnam et al. |
| 2011/0094513 A1 | | 4/2011 | Takatori et al. |
| 2011/0319783 A1 | | 12/2011 | Lindholt et al. |
| 2012/0285463 A1 | | 11/2012 | Dillingham et al. |
| 2013/0060157 A1 | | 3/2013 | Beard |
| 2013/0074845 A1 | | 3/2013 | Smith et al. |
| 2014/0283831 A1 | | 9/2014 | Foote et al. |
| 2015/0099986 A1 | | 4/2015 | Inoue |
| 2015/0128954 A1 | | 5/2015 | Smith et al. |
| 2015/0335843 A1 | | 11/2015 | Matsubara et al. |
| 2015/0335844 A1 | | 11/2015 | Matsubara et al. |
| 2015/0335847 A1 | | 11/2015 | Matsubara et al. |
| 2017/0196512 A1 | | 7/2017 | Inoue |
| 2018/0339123 A1 | | 11/2018 | Smith et al. |
| 2019/0099568 A1 | | 4/2019 | Foote et al. |
| 2019/0269872 A1 | | 9/2019 | Smith et al. |

FOREIGN PATENT DOCUMENTS

| | | |
|---|---|---|
| EP | 0053449 A1 | 6/1982 |
| EP | 2319569 A2 | 5/2011 |
| JP | 6292802 | 6/1987 |
| JP | 294566 | 7/1990 |
| JP | 2000-14785 A | 1/2000 |
| JP | 2001511035 | 8/2001 |
| JP | 2003533296 | 11/2003 |
| JP | 20040507333 | 11/2003 |
| JP | 3102973 | 7/2004 |
| JP | 20005253925 | 9/2005 |
| JP | 2005304574 | 11/2005 |
| JP | 2008500132 A | 1/2008 |
| JP | 2006068471 | 9/2008 |
| JP | 2009519759 | 5/2009 |
| JP | 2011-115543 A | 6/2011 |
| JP | 2014519948 A | 8/2014 |
| JP | 2015073751 A | 4/2015 |
| JP | 2016000157 A | 1/2016 |
| WO | 9829153 A1 | 7/1998 |
| WO | 0187394 A3 | 11/2001 |
| WO | 2006039788 A1 | 4/2006 |
| WO | 2007128100 A1 | 11/2007 |
| WO | 2008011682 A1 | 1/2008 |
| WO | 2009003488 A2 | 1/2009 |
| WO | 2009108995 A1 | 9/2009 |
| WO | 20180017565 A1 | 1/2018 |

OTHER PUBLICATIONS

English translation of Office Action for CN Application No. 201780045532.9, dated Jan. 4, 2021.
International Preliminary Report on Patentability dated Jan. 31, 2019 for PCT Application No. PCT/US2017/042582, 13 pages.
[English Translation] Notice of Reasons for Refusal for Japanese Patent Application No. 2019-524125, dated Aug. 10, 2021.
English translation of Office Action for JP Application No. 2019-524125, dated May 25, 2021.

* cited by examiner

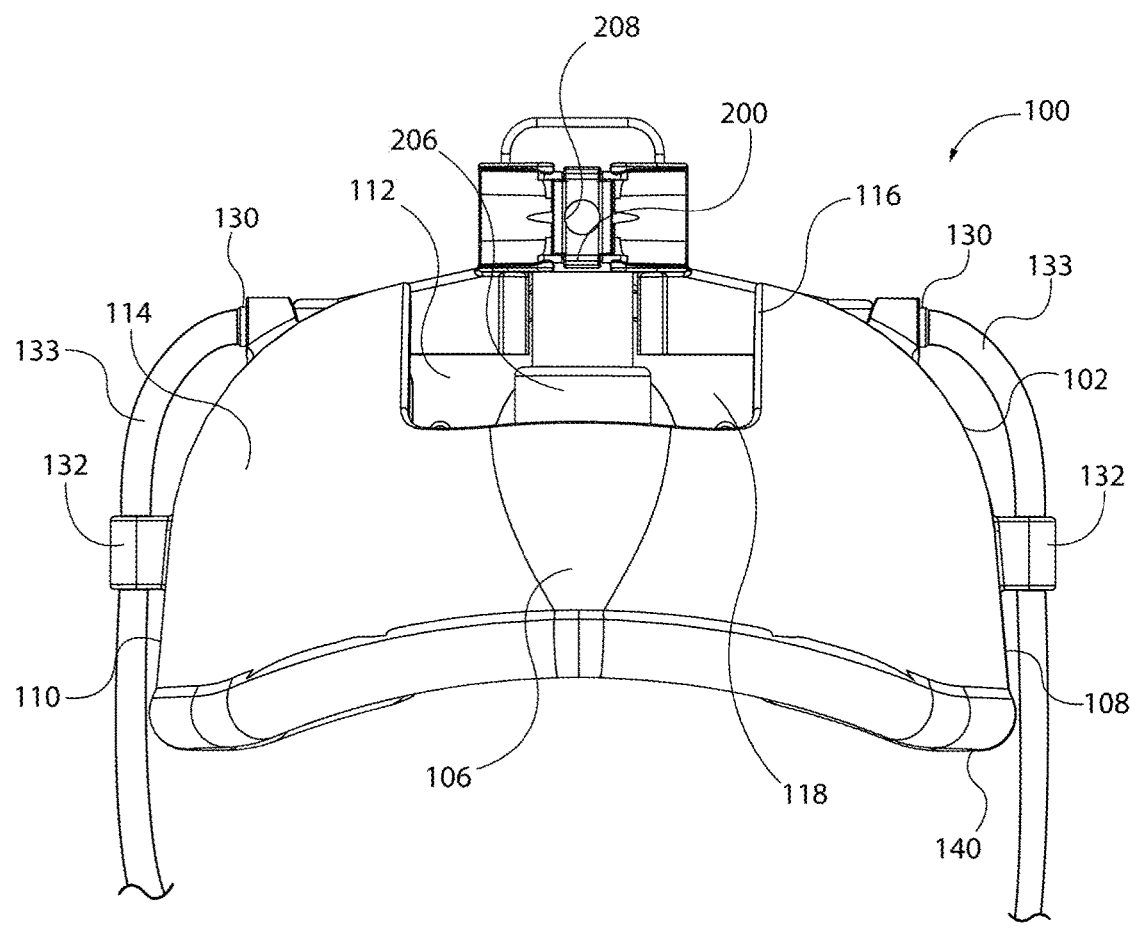
FIG. 5
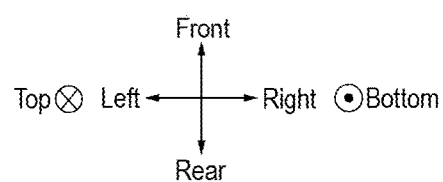

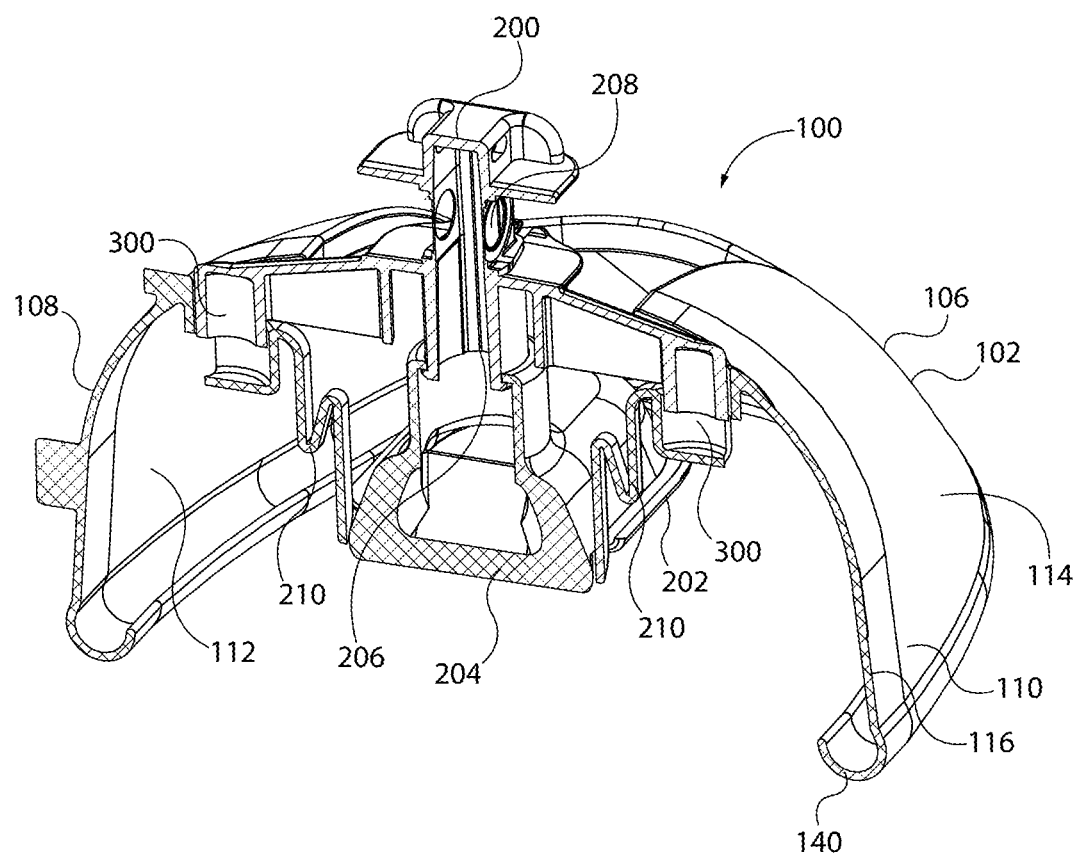
FIG. 9
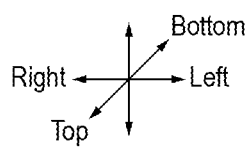

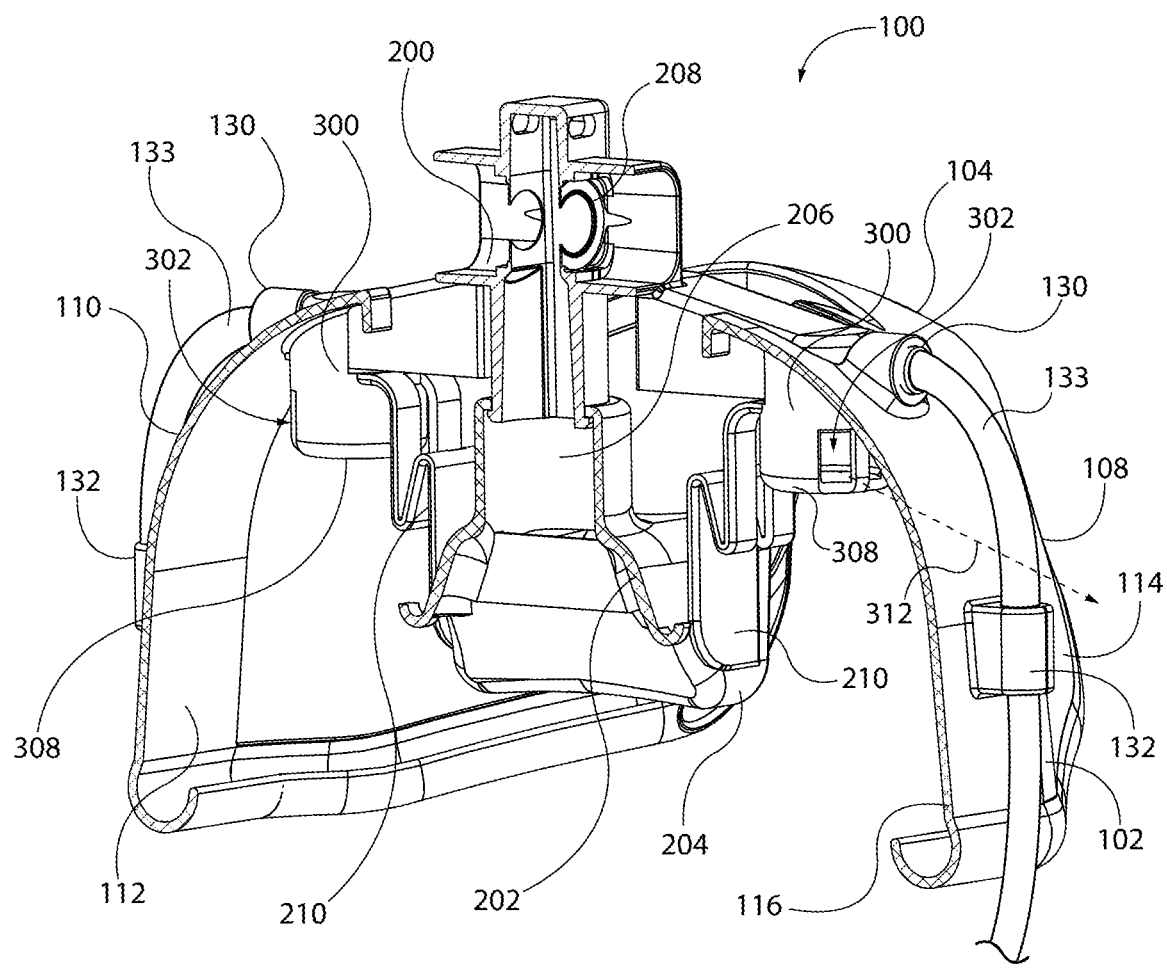
FIG. 11
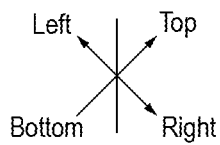

MASKS, SYSTEMS, AND METHODS FOR ASSISTING RESPIRATION INCLUDING SCATTERING CHAMBER

RELATED APPLICATIONS

This application is a U.S. National Stage filing under 35 U.S.C. § 371 of PCT Application No. PCT/US2017/042582, filed Jul. 18, 2017, which claims priority to U.S. Provisional Application No. 62/365,730, filed Jul. 22, 2016, which applications are incorporated herein by reference, in their entirety, for any purpose.

TECHNICAL FIELD

Examples described herein include masks which may be attached to the face of a patient so as to introduce a gas supply to the patient. Example masks may include scattering chambers which may facilitate diffusing incoming air supply away from direct impact on the patient's skin.

BACKGROUND

An oxygen supply mask may be connected adjacent a patient's facial skin to provide a supply of oxygen to the patient. The flow of supplied oxygen directly onto a patient's bare skin may be harmful to the patient, causing the patient discomfort and also drying and chilling the patient's skin. The patient's discomfort may lead to the constant adjustment or the eventual removal of the mask, which decreases the quality of the air inhaled by the patient and may impede the patient's recovery if undergoing a procedure.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

In an example, a mask is configured to assist the respiration of a patient and has a gas inlet port positioned to connect a gas supply to the mask and direct gas flow towards a patient's skin. There is a scattering chamber with an inlet port and a plurality of outlet ports, the scattering chamber inlet port fluidly connected to the gas inlet port, and the plurality of outlet ports positioned to scatter the gas flow away from the patient's skin and towards the interior surface of the mask and a region between the patient's skin and the interior surface of the mask. There is an outgas collector assembly connected adjacent the scattering chamber and positioned to collect an outgas emission expelled from the patient and eject the outgas emission from the mask.

An example method of protecting a patient's skin during supplemental respiration using a mask may include introducing gas to a gas supply inlet port of the mask, and the gas supply inlet port is positioned to direct the gas towards a patient's face. The gas may be diverted away from the patient's face by flowing the gas through a scattering chamber of the mask; and the patient's outgas may be collected in an outgas collector assembly when the patient exhales.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

FIG. 5 is a bottom plan view of the mask of FIG. 1;

FIG. 9 is a cross-sectional isometric elevation view of the mask of FIG. 6 shown along line 3-3, shown looking towards the bottom end of the mask with a partial view of the oral outgas collector;

FIG. 11 is a cross-sectional isometric elevation view of the mask of FIG. 6 shown along line 5-5, shown looking towards the top end of the mask with a partial view of the outgas collector channel;

Figure 1:
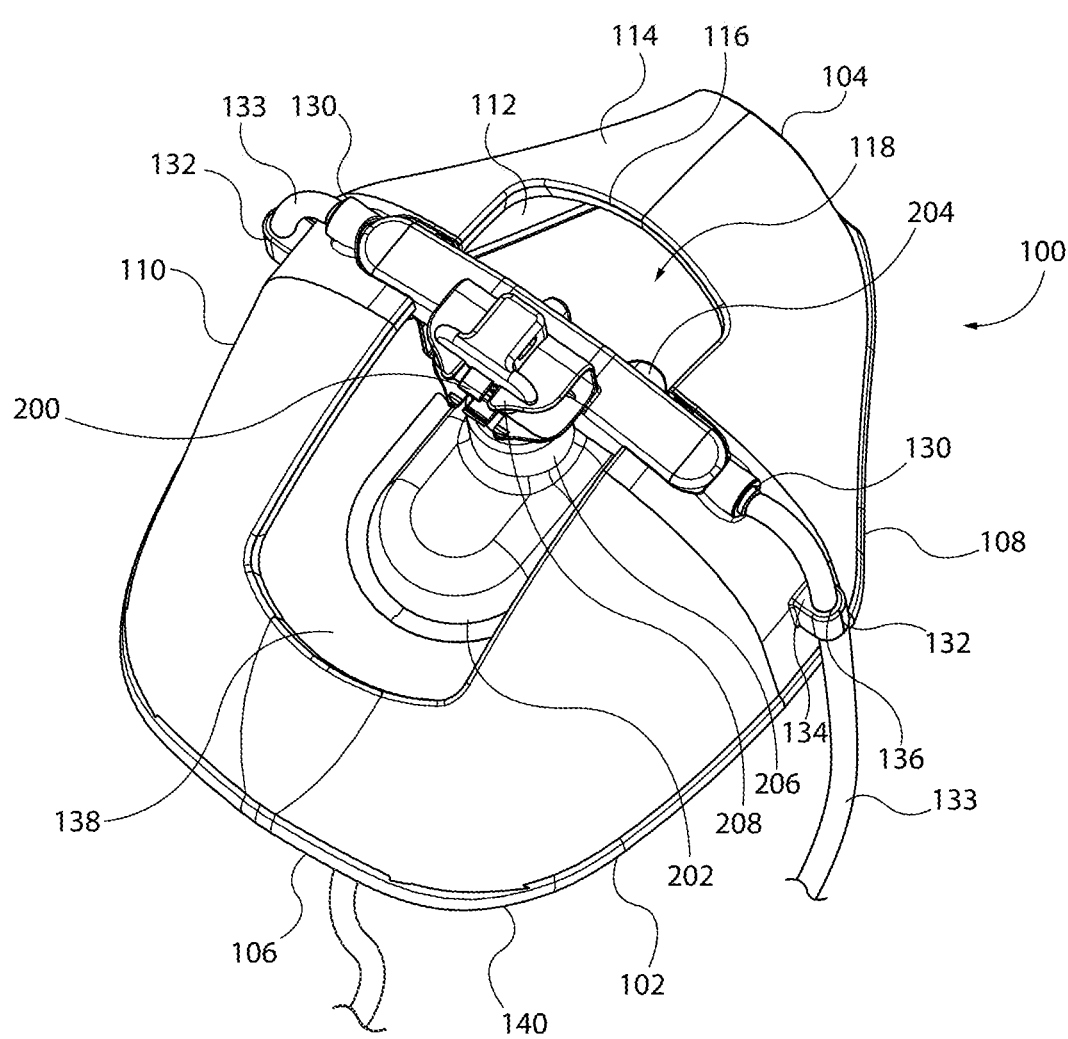
FIG. 1 is an isometric elevation view of a mask according to an embodiment of the presently disclosed subject matter.
Figure 1:
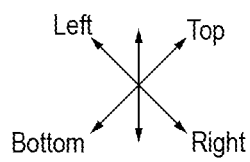

all arranged in accordance with at least some embodiments of the present disclosure.

DETAILED DESCRIPTION

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are implicitly contemplated herein.

This disclosure describes examples of methods, systems, products, devices, and/or apparatus generally related to a mask configured to assist the respiration of a patient. In one example, a mask may include a gas inlet port positioned to connect a gas supply to the mask and direct gas flow into a region between a patient's skin and an interior surface of the mask. The mask may further include a scattering chamber with an inlet port and a plurality of outlet ports, the scattering chamber inlet port fluidly connected to the gas inlet port, and the plurality of outlet ports positioned to scatter the gas flow away from the patient's skin and towards the interior surface of the mask. The mask may further include an outgas collector assembly connected adjacent the scattering chamber and positioned to collect an outgas emission expelled from the patient and eject the outgas emission from the mask.

FIG. 1 is an isometric elevation view of a mask according to an embodiment of the presently disclosed subject matter. FIG. 1 shows a mask 100; a shield 102 with a top end 104, a bottom end 106, a right side 108, a left side 110, an interior surface 112, an exterior surface 114, and a wall thickness 116; a rebreather aperture 118; an outgas collector assembly 200 with an oral outgas collector 202, a nasal outgas collector 204, an outgas collector channel 206, and an outgas collector analyzer 208; two gas supply inlet ports 130; two gas supply alignment features 132, each with a tab 134 and an aperture 136; two gas supply lines 133; a chamber 138; and a skin contacting portion 140.

The mask 100 of FIG. 1 may have a general dome shape appearance. Generally, any overall shape or appearance may be used. Typically, a shape may be used which conforms to a patient's face over the patient's mouth and/or nose. The mask 100 may include a shield 102 with a top end 104, a right side 108, a bottom end 106, and a left side 110. The shield may be formed of any of a variety of materials, such as plastic. The material used to form the shield may be transparent in some examples and may be flexible in some examples.

The shield may also have a skin contacting portion 140 that surrounds a bottom edge of the shield 102. The skin contacting portion 140 may include a rounded convex shape arcing away from the inside of the mask 100. In some examples, the skin contacting portion may be made from an additional material, such as a gasket material, that may improve sealing to a face of a patient.

The shield 102 may have an interior surface 112 and exterior surface 114. A chamber 138 may be formed between the interior surface 112 of the shield 102, a rebreather aperture 118, and the patient's skin. The chamber 138 may act as a mixing chamber to control or direct the mixture of air being inhaled by the patient and also to keep the mixture of air in a breathable area for the patient. In some examples, the chamber 138 may be shaped such that a supplied gas is reflected off of the interior surface 112 and mixed with ambient air prior to being inhaled by the patient. In some examples, a portion of the patient's exhaled outgas may enter the chamber 138 and is mixed with ambient air and supplied gas prior to the re-inhalation by the patient.

A rebreather aperture 118 may be formed by the edges of the top end 104, left side 110, bottom end 106, and right side 108 of the shield 102. The rebreather aperture 118 may help reduce or prevent the patient's expelled outgas from being directly re-inhaled. The rebreather aperture 118 allows ambient air to be fluidly connected to the chamber 138. The rebreather aperture 118 may help dilute any expelled outgas by mixing with ambient air and supplied gas prior to re-inhalation by the patient. In an example, the rebreather aperture is rectangular shaped with longer edges adjacent the right side 108 and left side 110 of the shield 102, and with curved, shorter edges adjacent the top end 104 and bottom end 106 of the shield 102. Different patients may have different facial shapes and different rebreather needs. To accommodate these parameters, different examples of the rebreather aperture may be reduced, enlarged or the shape itself may be changed.

The mask 100 may have two gas supply inlet ports 130 which may be used to connect a gas supply flowing through two gas supply lines 133 to the mask 100 and direct the gas flow into the chamber 138. While two gas supply inlet ports 130 are shown in FIG. 1, any number may be provided in other examples, including 1 gas supply inlet port, 3 gas supply inlet ports, or 4 gas supply inlet ports. In an embodiment, the gas supply inlet ports 130 are cylindrical, although other cross-sectional shapes may be used. The mask 100 may include two gas supply alignment features 132 located on the right side 108 and the left side 110. A gas supply may be provided, for example, from a pressurized tank or other source of gas. Any of a variety of gas supplies may be used with masks described herein. Example gas supplies include, but are not limited to, oxygen, nitrogen, oxygen blends, nitrous oxide, or combinations thereof. A gas supply line may run from the tank to the gas supply inlet ports 130, and may be coupled to the gas supply alignment feature 132.

Each gas supply alignment feature 132 may include a tab 134 and an aperture 136. In an embodiment, the aperture 136 is circular, although other cross-sections may be used in other examples. The two gas supply alignment features 132 may be used to secure a gas supply line 133 to the mask 100 to aid in patient comfort and to ensure the gas supply line 133 remains connected to the mask 100. For example, a gas supply line 133 may be routed through the aperture 136 and connected to the gas supply inlet port 130.

The mask 100 may be placed on the face of a patient such that the mask may partially cover the patient's oral and/or nasal passages. The shield 102 may be made from a flexible material that will help the various sides and ends to adjust to the various shapes of a patient's facial structure. The top end 104 may be shaped to flexibly accommodate the various shapes of a patient's nose. The right side 108 and left side 110 may be shaped to flexibly accommodate the various shapes of a patient's cheeks, and the bottom end 106 may be shaped to flexibly accommodate the various shapes of a patient's chin. The skin contacting portion 140 contacts the patient's facial skin. In some examples, the rounded convex shape of the skin contacting portion 140 allows for the mask 100 to comfortably contact the patient's skin. In addition, the curved shape of the skin contacting portion 140 may reduce or prevent the escape of supplied gas from the chamber 138, such that the gas does not flow, or the flow is reduced, between the skin contacting portion 140 and the patient's skin.

An outgas collector assembly 200 may span the rebreather aperture 118 and may be connected to the right side 108 and left side 110 of the mask 100. The outgas collector assembly 200 may have an oral outgas collector 202 positioned adjacent to the patient's oral passage to collect some or all of the patient's oral outgas emissions. The outgas collector assembly 200 may additionally or instead have a nasal outgas collector 204 positioned adjacent to at least one of the patient's nasal passage to collect the patient's nasal outgas emissions. The outgas collector assembly 200 is connected to a scattering chamber 300 (shown in FIG. 3) and positioned to collect an outgas emission expelled from the patient and eject the outgas emission from the mask 100.

In some examples, the oral outgas collector 202 does not directly contact the patient's skin, such that a gap is formed between the bottom of the oral outgas collector 202 and the patient's oral passage. Any size gaps may be used—on the order of millimeters in some examples, centimeters in some examples. The gap may help to ensure that fresh gas from the gas supply may flow towards the patient's oral passage. In an embodiment, the nasal outgas collector 204 does not directly contact the patient's skin, such that a gap is formed between the bottom of the nasal outgas collector 204 and at least one of the patient's nasal passage. Despite the outgas collection using the oral outgas collector 202 and nasal outgas collector 204, additional outgas expelled from the patient may flow into the chamber 138 created between the interior surface 112 of the shield 102 and the patient's skin Inhaling expelled outgas may be harmful to a patient, and the rebreather aperture 118 may allow the chamber 138 to fluidly connect with ambient air, such that any expelled outgas located within the chamber 138 may be diluted with ambient air and supplied gas prior to inhalation by the patient.

In an embodiment, the outgas collector assembly 200 may be removable. This may be desired so that medical personnel may examine a patient's oral and nasal passageways without removing the entire mask. In some examples, the outgas collector assembly 200, with the oral outgas collector 202, nasal outgas collector 204, an outgas collector channel 206, and an outgas collector analyzer 208 may be disconnected from the mask 100 and removed so that the patient's oral and nasal passages are exposed through the rebreather aperture 118. Through the rebreather aperture 118, medical personnel have access to examine the patient's oral and nasal passageways. The disconnection of the outgas collector assembly 200 does not disrupt the gas being supplied to the gas supply inlet ports 130 through the gas supply lines 133, such that a flow of supply gas may still be provided to assist the patient in respiration.

The various components described in FIG. 1 are merely examples, and other variations, including eliminating components, combining components, and substituting components are all contemplated.

Figure 2:
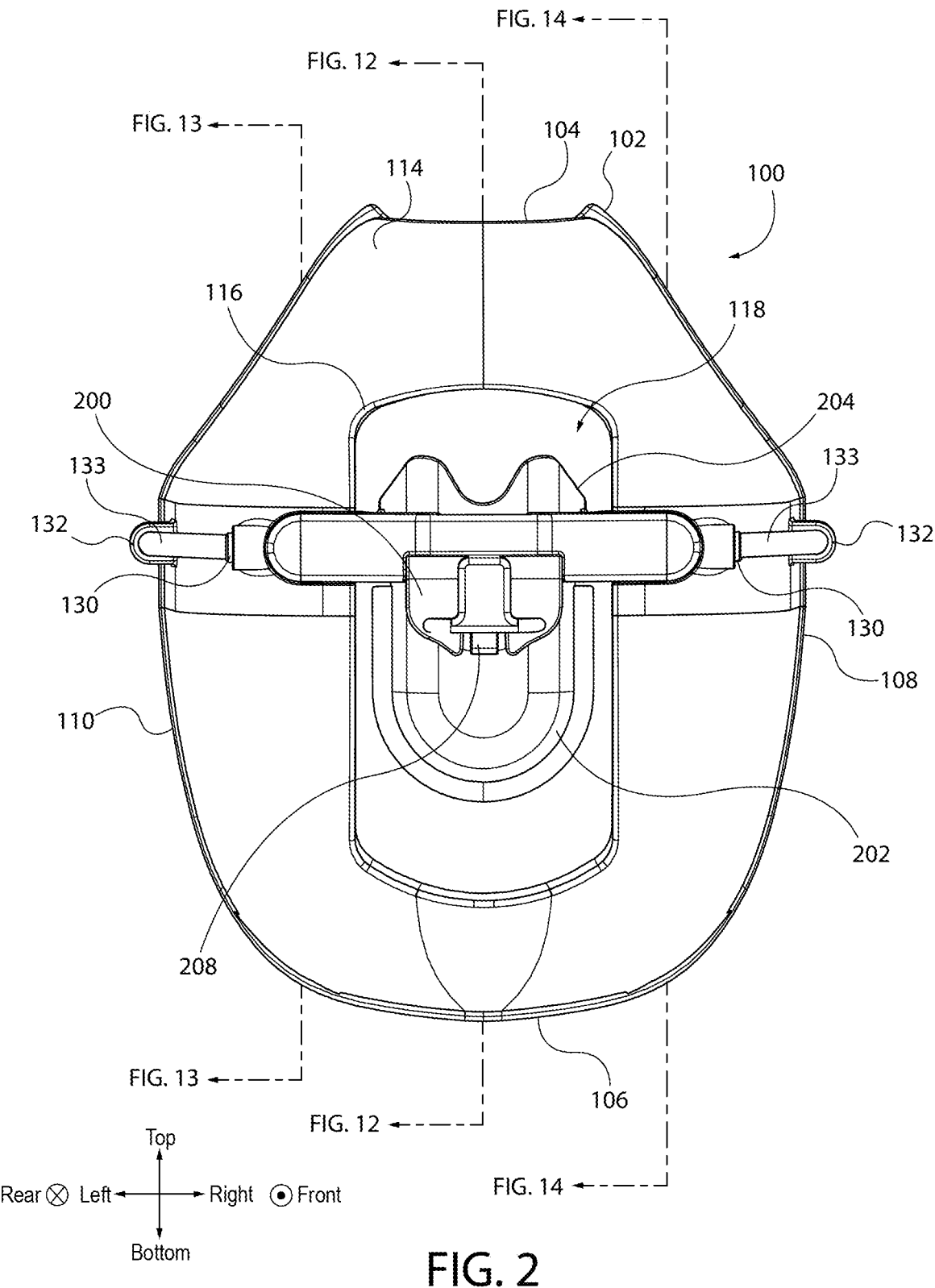
FIG. 2 is a front elevation view the mask of FIG. 1.

FIG. 2 is a front elevation view the mask of FIG. 1. FIG. 2 shows a mask 100; a shield 102 with a top end 104, a bottom end 106, a right side 108, a left side 110, an exterior surface 114, and a wall thickness 116; a rebreather aperture 118; an outgas collector assembly 200 with an oral outgas collector 202, a nasal outgas collector 204, and an outgas collector analyzer 208; two gas supply inlet ports 130; two gas supply lines 133; and two gas supply alignment features 132. The various components described in FIG. 2 are merely examples, and other variations, including eliminating components, combining components, and substituting components are all contemplated.

Figure 3:
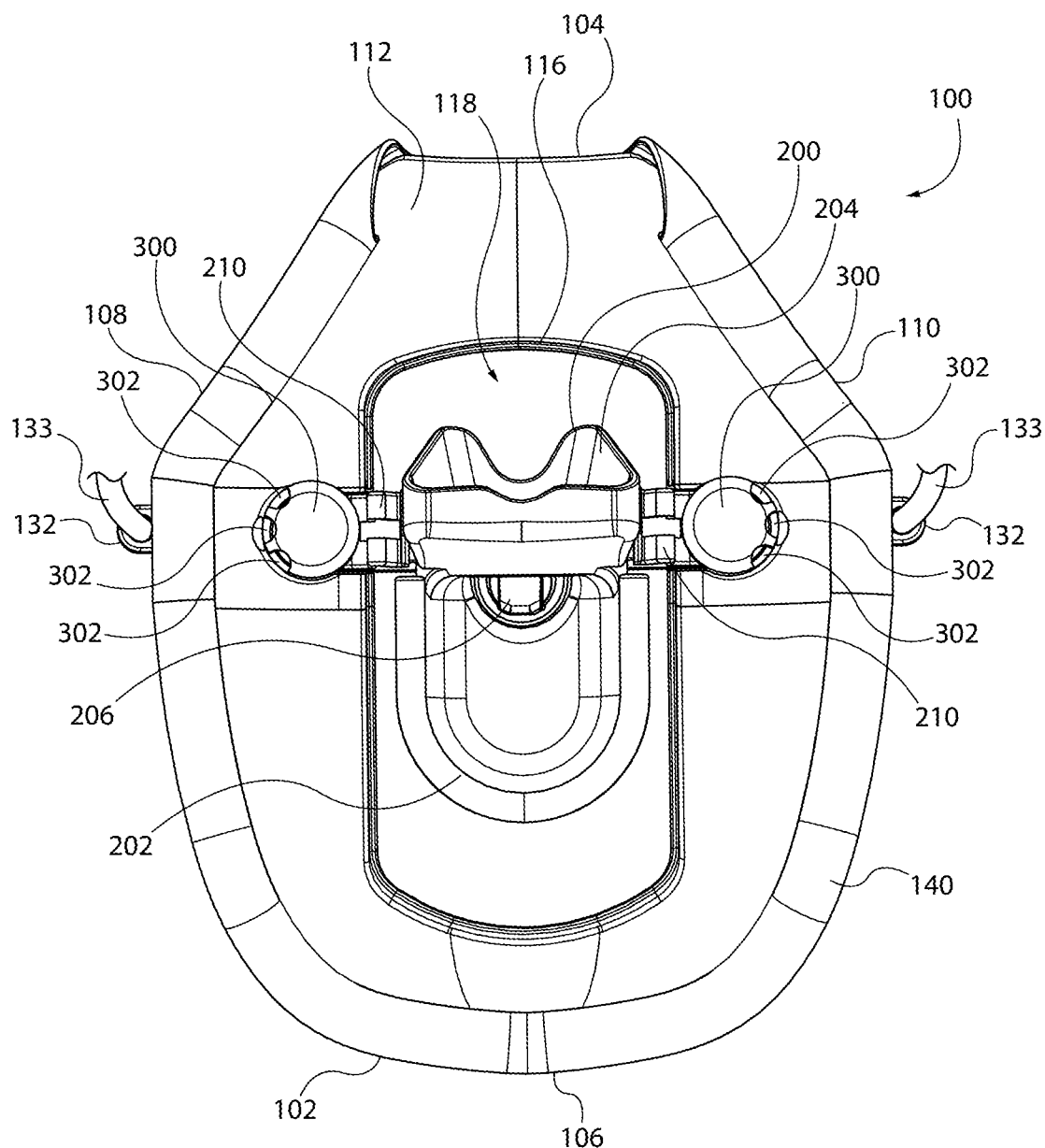
FIG. 3 is a rear elevation view of the mask of FIG. 1.

FIG. 3 is a rear elevation view of the mask of FIG. 1. FIG. 3 shows a mask 100; a shield 102 with a top end 104, a bottom end 106, a right side 108, a left side 110, an interior surface 112, an exterior surface 114, and a wall thickness 116; a rebreather aperture 118; an outgas collector assembly 200 with an oral outgas collector 202, a nasal outgas collector 204, and an outgas collector channel 206; two gas supply alignment features 132; two gas supply lines 133; a scattering chamber 300 with a plurality of scattering chamber outlet ports 302; two flexible members 210, and a skin contacting portion 140.

FIG. 3 shows two scattering chambers 300. The scattering chambers 300 are each fluidly connected to gas supply inlet ports 130 (e.g. the ports 130 shown in FIGS. 1 and 2). In an example, a gas flowing into the gas supply inlet port 130 will enter the corresponding scattering chamber 300, and will flow through and exit the chamber through the scattering chamber outlet ports 302. There may be any number of scattering chambers, with generally one scattering chamber provided per inlet port. In some examples, multiple inlet ports may be directed into a single scattering chamber. The scattering chambers 300 may serve to scatter the gas flow away from the patient's skin (e.g. not directly toward the patient's skin) and towards the interior surface 112 of the mask 100.

The plurality of scattering chamber outlet ports 302 are positioned to scatter the gas flow away from the patient's skin and towards the interior surface 112 of the mask 100. There may be any number of outlet ports. The outlet ports may be slots, holes, or any other shaped aperture. Generally, the aperture are position such that gas flowing through them is directed away (e.g. not directly toward) the patient's face. In this manner, gas may be introduced to an interior of the mask without being directed directly towards a patient's skin. For example, by scattering the gas flow away from the patient's skin, generally the gas flow is directed in a direction which is not perpendicular to the patient's nearby skin surface. The interior surface 112 of the mask 100 may be positioned to reflect the scattered gas supply flow back towards to a patient's oral and nasal passage for inhalation of the gas by the patient.

The various components described in FIG. 3 are merely examples, and other variations, including eliminating components, combining components, and substituting components are all contemplated.

Figure 4:
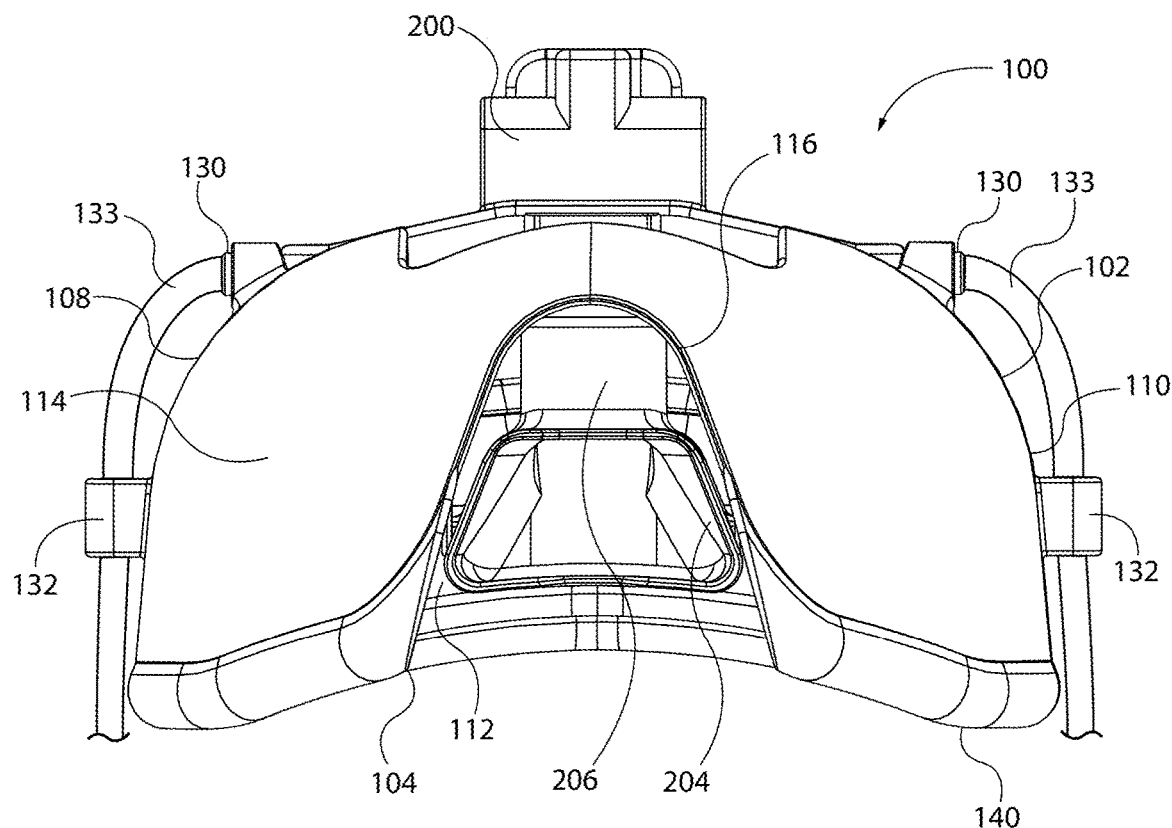
FIG. 4 is a top plan view of the mask of FIG. 1.

FIG. 4 is a top plan view of the mask of FIG. 1. FIG. 4 shows a mask 100; a shield 102 with a top end 104, a right side 108, a left side 110, an interior surface 112, an exterior surface 114, and a wall thickness 116; an outgas collector assembly 200 with a nasal outgas collector 204, and an outgas collector channel 206; two gas supply inlet ports 130; two gas supply alignment features 132; two gas supply lines 133; and a skin contacting portion 140. The various components described in FIG. 4 are merely examples, and other variations, including eliminating components, combining components, and substituting components are all contemplated.

FIG. 5 is a bottom plan view of the mask of FIG. 1. FIG. 5 shows a mask 100; a shield 102 with a bottom end 106, a right side 108, a left side 110, an interior surface 112, an exterior surface 114, and a wall thickness 116; an outgas collector assembly 200 with an outgas collector channel 206, and outgas collector analyzer 208; two gas supply inlet ports 130; two gas supply alignment features 132; two gas supply lines 133; a rebreather aperture 118; and a skin contacting portion 140.

The outgas collector analyzer 208 may be used to connect a gas composition sensor to the outgas collector channel 206 or to a different part of the outgas collector assembly 200. This may enable the measurement of the outgas exhausted from the patient prior to the outgas being exhausted from the outgas collector assembly 200. In some examples, the outgas collector analyzer 208 may include an analyzer so that the composition of the patient's outgas may be measured. The analyzer may be implemented, for example, using a gas detector. This may be desirable so that an accurate emission composition of the patient's exhausted outgas may be measured prior to the outgas being diluted or significantly diluted with ambient air. The various components described in FIG. 5 are merely examples, and other variations, including eliminating components, combining components, and substituting components are all contemplated.

Figure 6:
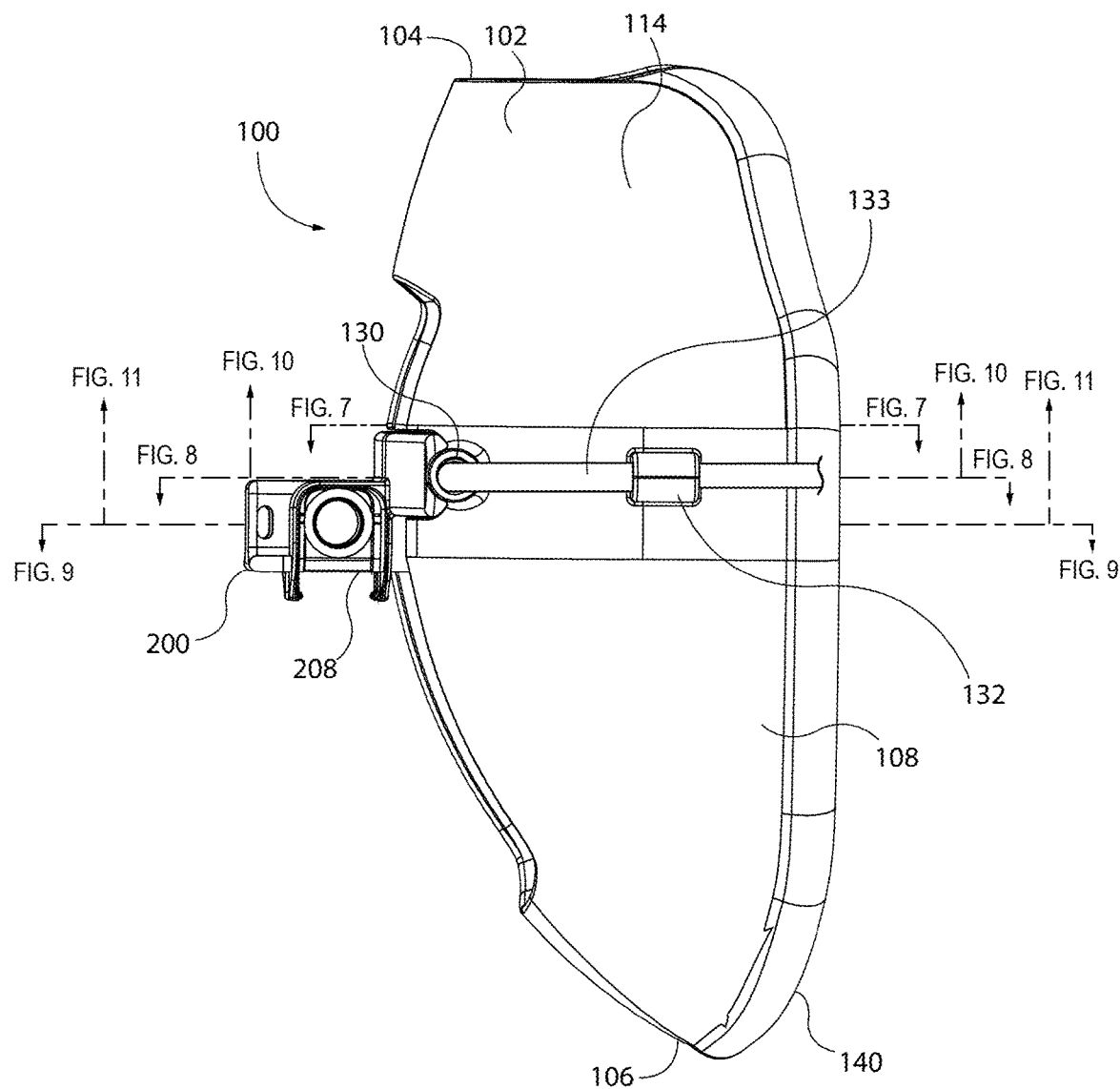
FIG. 6 is a right side elevation view of the mask of FIG. 1.
Figure 6:
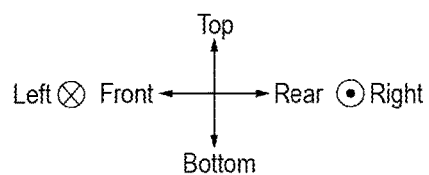

FIG. 6 is a right side elevation view of the mask of FIG. 1. FIG. 6 shows a mask 100; a shield 102 with a top end 104, a bottom end 106, a right side 108, and an exterior surface 114; an outgas collector assembly 200 with an outgas collector analyzer feature 208; a gas supply inlet port 130; a gas supply alignment feature 132; a gas supply line 133; and a skin contacting portion 140. The various components described in FIG. 6 are merely examples, and other variations, including eliminating components, combining components, and substituting components are all contemplated.

Figure 7:
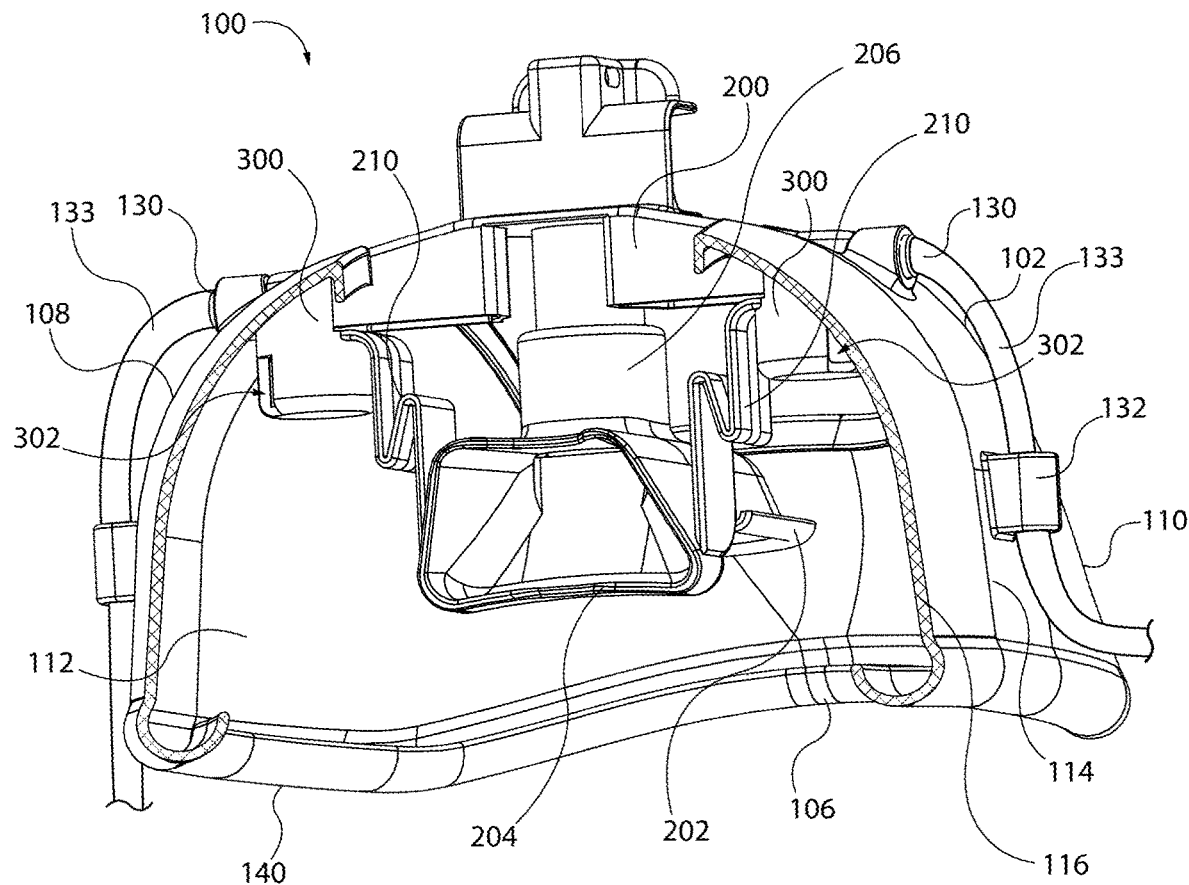
FIG. 7 is a cross-sectional isometric elevation view of the mask of FIG. 6 shown along line 1-1, shown looking towards the bottom end of the mask with a partial view of the nasal outgas collector.

FIG. 7 is a cross-sectional isometric elevation view of the mask of FIG. 6 shown along line 1-1, shown looking towards the bottom end of the mask with a partial view of the nasal outgas collector. FIG. 7 shows a mask 100; a shield 102 with a bottom end 106, a right side 108, a left side 110, an interior surface 112, an exterior surface 114, and a wall thickness 116; a skin contacting portion 140; two gas supply inlet ports 130; a gas supply alignment feature 132; two gas supply lines 133; an outgas collector assembly 200 with an outgas collector channel 206, an oral outgas collector 202, a nasal outgas collector 204; two flexible members 210; and two scattering chambers 300 with scattering chamber outlet ports 302.

The flexible members 210 may be connected to an external surface of the scattering chambers 300 and the nasal outgas collector 204. The flexible members 210 may be used to adjustably position the oral outgas collector 202 and the nasal outgas collector 204 within the mask 100 to accommodate various patient's facial shapes and comfort needs. The oral outgas collector 202 and the nasal outgas collector 204 are fluidly connected to the outgas collector channel 206 such that the outgas emissions from a patient's oral and nasal passages are collected and combined prior to being exhausted out of the mask 100. The various components described in FIG. 7 are merely examples, and other variations, including eliminating components, combining components, and substituting components are all contemplated.

Figure 8A:
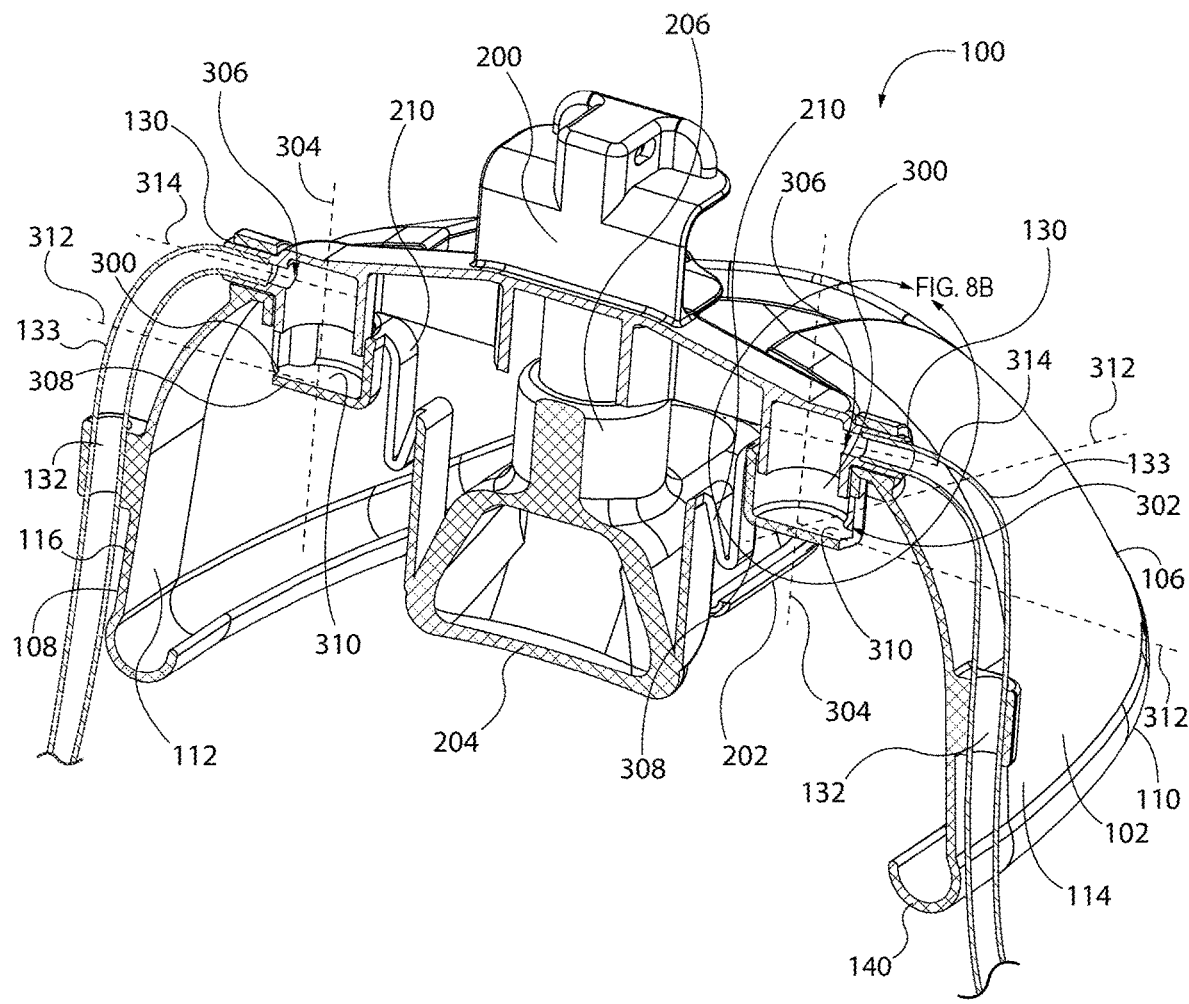
FIG. 8A is a cross-sectional isometric elevation view of the mask of FIG. 6 shown along line 2-2, shown looking towards the bottom end of the mask with a partial view of the nasal outgas collector and scattering chamber.
Figure 8A:
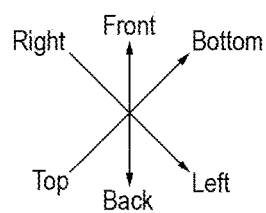

FIG. 8A is a cross-sectional isometric elevation view of the mask of FIG. 6 shown along line 2-2, shown looking towards the bottom end of the mask with a partial view of the nasal outgas collector and scattering chamber. FIG. 8A shows a mask 100; a shield 102 with a bottom end 106, a right side 108, a left side 110, an interior surface 112, an exterior surface 114, and a wall thickness 116; a skin contacting portion 140; two gas supply inlet ports 130; two gas supply alignment features 132; two gas supply lines 133; an outgas collector assembly 200 with an outgas collector channel 206, an oral outgas collector 202, and a nasal outgas collector 204; two flexible members 210; and two scattering chambers 300, each with a central axis 304, an scattering chamber inlet port 306 with a central axis 314, a flow deflector 308 with a top surface 310, and scattering chamber outlet ports 302, each with a central axis 312.

The scattering chambers 300 may serve to scatter the gas flow away from the patient's skin (e.g. not directly toward the patient's skin) and towards the interior surface 112 of the mask 100. By scattering the gas flow away from the patient's skin, generally the gas flow is directed in a direction which is not perpendicular to the patient's nearby skin surface. The interior surface 112 of the mask 100 may be positioned to reflect the scattered gas supply flow back towards to a patient's oral and nasal passage for inhalation of the gas by the patient. In an embodiment, the interior surface 112 may also include a sensor to measure the air composition near the interior surface 112 of the mask 100.

The reflection of the scattered gas supply may also promote the mixing of the scattered gas supply with ambient air supplied from the rebreather aperture 118, such that scattered flow that comes into contact with a patient's skin may have a decreased undesirable effect on the skin. The spacing between the patient's oral passageway and the oral outgas collector 202, and between the patient's nasal passageway and the nasal outgas collector 204 may further promote the availability of the scattered gas supply flow for patient inhalation.

Each scattering chamber 300 may have a central axis 304, a scattering chamber inlet port 306 with a central axis 314, a flow deflector 308 with a top surface 310, and a plurality of scattering chamber outlet ports 302, each with a central axis 312.

The flow deflector 308 may be formed as a bottom portion of the scattering chamber 300 or it may be a separate part assembled or connected with the scattering chamber 300. In an embodiment, the top surface 310 of the flow deflector 308 is positioned to direct the gas supply flow from the scattering chamber inlet port 306 to the scattering chamber outlet ports 302. In the embodiment shown in FIGS. 8A and 8B, the flow deflector 308 has a cylindrical shape and its top surface 310 is generally flat and substantially perpendicular to the central axis 304 of the scattering chamber 300. In an alternate embodiment, the flow deflector 308 may be shaped such that the top surface 310 is not generally flat such that it may have an undulating or sloped surface.

Each scattering chamber 300 is positioned to be fluidly connected with the gas supply inlet port 130. In an embodiment, the gas supply flowing into the scattering chamber 300 enters the chamber through the scattering chamber inlet port 306, flows through a central portion of the scattering chamber 300, strikes the top surface 310 of the flow deflector 308 where the flow is then deflected out of the scattering chamber outlet ports 302 and into the chamber 138 towards the interior surface 112 of the mask 100. The various components described in FIG. 8A are merely examples, and other variations, including eliminating components, combining components, and substituting components are all contemplated.

Figure 8B:
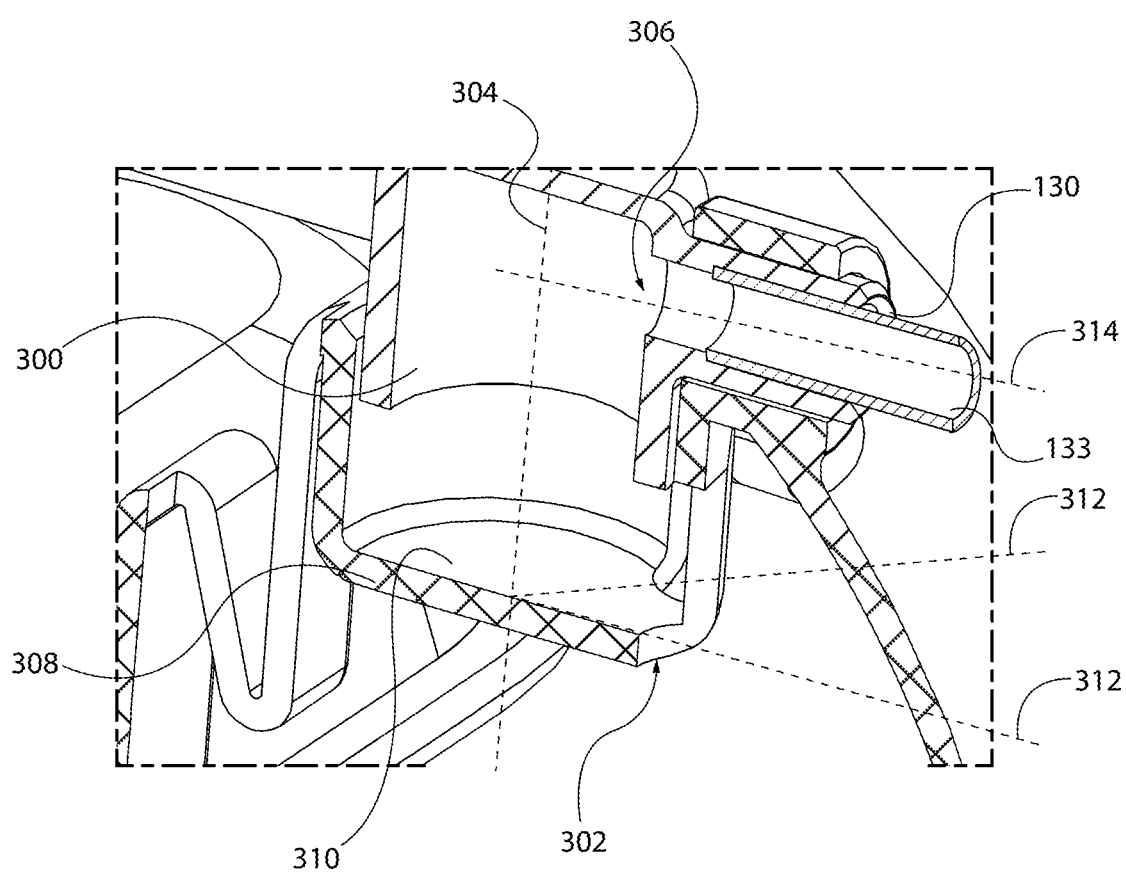
FIG. 8B is an enlarged view of the scattering chamber portion of the mask of FIG. 8A.

FIG. 8B is an enlarged view of the scattering chamber 300 of the mask of FIG. 8A. FIG. 8B shows a gas supply inlet port 130, a gas supply line 133; and a scattering chamber 300 with a central axis 304, a scattering chamber inlet port 306 with a central axis 314, a plurality of scattering chamber outlet ports 302, each with a central axis 312, and a flow deflector 308 with a top surface 310.

As described in relation to embodiment of FIG. 8A, the gas supply flowing into the scattering chamber 300 enters the chamber through the scattering chamber inlet port 306, flows through a central portion of the scattering chamber 300 along a path substantially parallel to the central axis 304, and is then deflected off of the flow deflector 308 to then exit the chamber through the scattering chamber outlet ports 302.

In the embodiment of FIG. 8B, the scattering chamber inlet port 306 has a central axis 314 that is substantially normal to the central axis 304 of the scattering chamber 300 and parallel to the top surface 310 of the flow deflector 308. The normal alignment of the central axis 304 and the central axis 314 may cause the supplied gas to be deflected off of an inner surface of an upper portion of the scattering chamber 300 so that the flow then becomes substantially parallel to the central axis 304. A flow substantially parallel to the central axis 304 may help ensure that the flow is later more completely deflected off of the flow deflector 308 prior to exiting the scattering chamber 300, which may direct more of the flow towards an inner interior surface 112 of the mask as opposed to directly towards the patient's skin. This could be desirable when a lower volumetric flow rate of gas is immediately needed by a patient, such as when the patient weighs less or when the patient's respiratory medical needs do not dictate a significant supplement of supplied gas in addition to ambient air.

In some examples, the angle between central axis 304 and the central axis 314 may be greater than normal, such that more of the initial flow of supplied gas is immediately directed towards the bottom portion of the scattering chamber 300 or directly out of the scattering chamber outlet ports 302. This could be desirable when a higher volumetric flow rate of gas is immediately needed by the patient, such as when the patient weighs more and therefor requires a larger volume of gas, or when the patient's respiratory medical needs dictate a larger volume of supplied gas.

In some examples, the angle between central axis 304 and the central axis 314 may be less than normal, such that more of the initial flow of supplied gas is directed towards an upper portion of the scattering chamber 300. This would enhance the mixing of the supplied gas with ambient air within the scattering chamber 300. This could be desirable when a lower volumetric flow rate of gas is immediately needed by a patient, such as when the patient weighs less or when the patient's respiratory medical needs do not dictate a significant supplement of supplied gas in addition to ambient air.

The direction of the deflected flow out of the scattering chamber outlet ports 302 may be determined in part by the shape of the flow deflector 308 and the location of the scattering chamber outlet ports 302. Each of the scattering chamber outlet ports 302 may be an aperture formed in the wall of the scattering chamber 300. In this embodiment, the central axis of each outlet port 302 may be parallel with the top surface 310 of the flow deflector 308. This may cause the deflected flow to exit the outlet port at an angle substantially normal to the central axis 304 of the scattering chamber 300, and be substantially directed towards the interior surface 112 of the mask, as opposed to towards the patient's skin. This could be desirable when a lower volumetric flow rate of gas is immediately needed by a patient, such as when the patient weighs less or when the patient's respiratory medical needs do not dictate a significant supplement of supplied gas supplied in addition to ambient air.

As shown in FIG. 8B, the scattering chamber outlet ports 302 may be apertures formed in the wall of the scattering chamber 300 and also in the flow deflector 308. The outlet ports may be rectangular, circular, or elliptical apertures, or combinations thereof. In the embodiment of FIG. 8B, the central axis 312 of the outlet port 302 may be obtuse when measured from the junction of the central axis 304 and the inlet port central axis 314. This position of the outlet port 302 may direct the gas supply flow out of the scattering chamber 300 slightly downward towards the patient's skin. This could be desirable when a higher volumetric flow rate of gas is immediately needed by the patient, such as when the patient weighs more and therefor requires a larger volume of gas, or when the patient's respiratory medical needs dictate a larger amount of supplied gas.

As shown in FIG. 8B, the scattering chamber outlet ports 302 of each scattering chamber 300 are positioned on the side of the scattering chamber 300 closest to the interior surface 112 of the mask 100, as opposed to the side closest to the outgas collector assembly. This arrangement may help deflect in some examples the flow of supplied gas away from the patient's oral and nasal passages so that it may be mixed with ambient air accessed through the rebreather aperture 118 of the mask 100 prior to inhalation by the patient. This arrangement may also help prevent in some examples the supplied gas from being "short-circuited" such that it is caught in the flow of exhausted outgas from the patient and is never inhaled by the patient. This prevention may be desired so that the patient receives the desired amount of supplied gas, so that the supplied gas is not wasted, or so that the outgas composition is not unnecessarily diluted by the addition of the supplied gas prior to measuring the composition of the patient's outgas via the outgas collector analyzer 208.

The cross-sectional area of the plurality of output ports may be selected based at least in part, on a desired volumetric flow rate. The volumetric flow rate of a system is a measure of the volume of fluid passing a point in the system per unit of time. The volumetric flow rate can be calculated as a product of the cross-sectional area for flow and the average flow velocity. For example, if the given average supplied gas flow velocity is held constant, an outlet port with a larger cross sectional area will allow a larger amount of gas flow over the same duration of time as compared to an outlet port with a smaller cross sectional area. A larger gas flow will supply a larger amount of gas to a patient, while a smaller gas flow will supply a smaller amount of gas to the patient.

It is also contemplated that the cross-sectional area of the scattering chamber outlet ports 302 may be adjusted so that the flow of supplied gas out of the outlet ports is adjusted. For example, it is contemplated that the scattering chamber 300 may have an adjustable member to allow for the adjustment of the flow of the gas supply through the scattering chamber 300. The adjustable member may be rotatably adjacent or slidably to at least one scattering chamber outlet port 302. For example, the adjustable member could be a sleeve that fits around the lower portion of the scattering chamber, and has outlet ports similar to those of the scattering chamber outlet port 302. The adjustable member may be slidably or rotatably adjusted so that its outlet ports completely align with the scattering chamber outlet ports 302, such that the scattering chamber outlet ports 302 are unblocked. The adjustable member may be adjusted so that it blocks a portion of the scattering chamber outlet ports 302, such that the flow through the scattering chamber outlet ports 302 is decreased.

In an embodiment, the scattering chamber 300 may be formed so that the position of the flow deflector 308 is adjustable as to augment the cross-sectional area of the scattering chamber outlet ports 302. The flow deflector 308 may be rotatably or slidably adjustable within the scattering chamber 300 so that the flow of supplied gas out of the scattering chamber outlet ports 302 is adjusted. In an example, the flow deflector 308 may be adjusted vertically upwards towards the interior surface 112 or downwards away from the interior surface 112, this changing the cross-sectional area of the outlet ports. In an example, the flow deflector may have an extending edge is substantially perpendicular to the top surface 310 and is centered about the central axis 304 of the scattering chamber 300, and the adjustment of the flow deflector 308 vertically upwards or downwards causes the extending edge to block or unblocks the scattering chamber outlet ports 302.

The various components described in FIG. 8B are merely examples, and other variations, including eliminating components, combining components, and substituting components are all contemplated.

FIG. 9 is a cross-sectional isometric elevation view of the mask of FIG. 6 shown along line 3-3, shown looking towards the bottom end of the mask with a partial view of the oral outgas collector. FIG. 9 shows a mask 100; a shield 102 with a bottom end 106, a right side 108, a left side 110, an interior surface 112, exterior surface 114, and a wall thickness 116; a skin contacting portion 140; an outgas collector assembly 200 with an outgas collector channel 206, an outgas collector analyzer 208, an oral outgas collector 202, and a nasal outgas collector 204; two flexible members 210; and two scattering chambers 300.

The embodiment of FIG. 9 shows the fluid connection between the oral outgas collector 202, the nasal outgas collector 204, and the scattering chamber inlet port 306. The various components described in FIG. 9 are merely examples, and other variations, including eliminating components, combining components, and substituting components are all contemplated.

Figure 10:
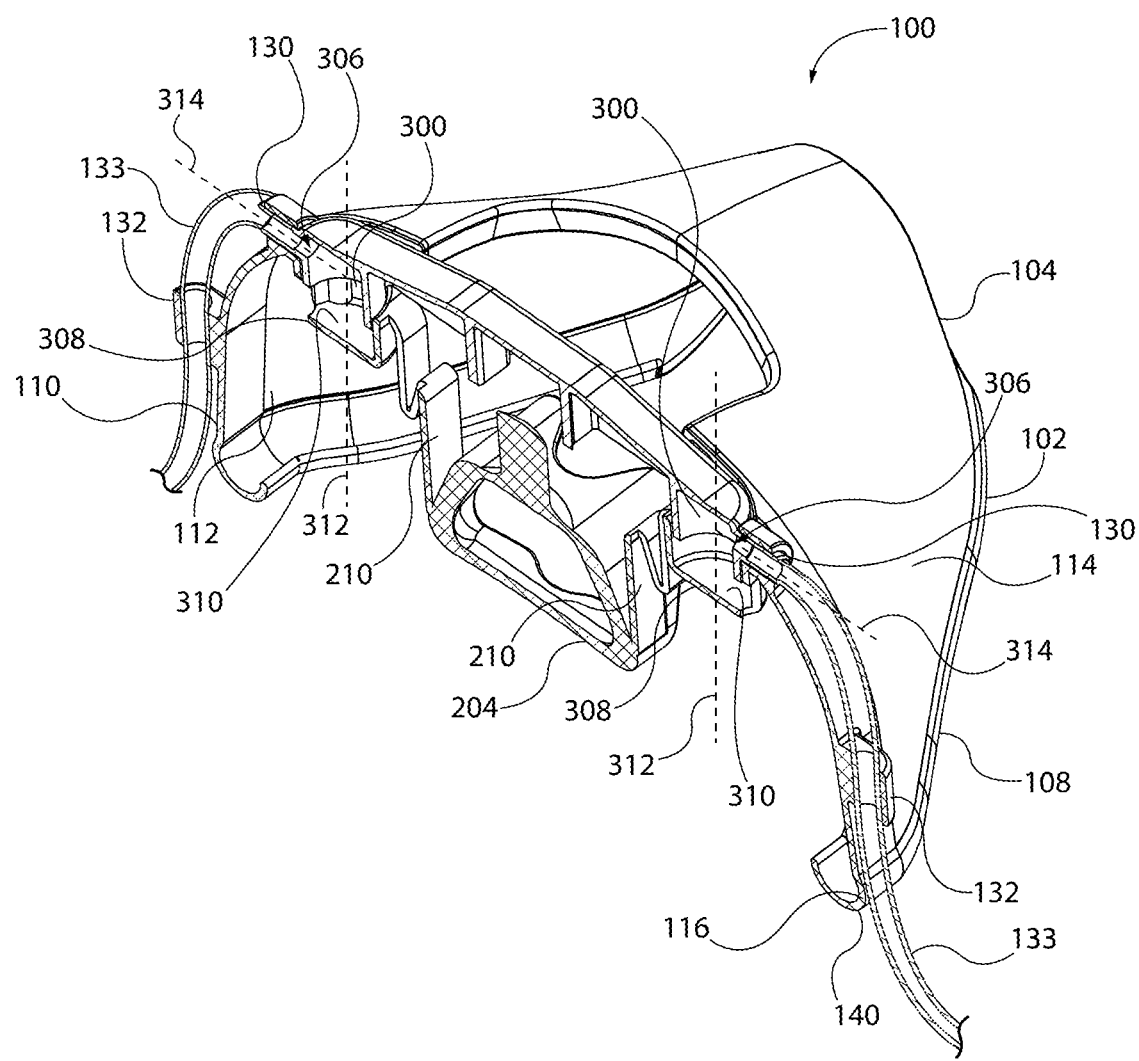
FIG. 10 is a cross-sectional isometric elevation view of the mask of FIG. 6 shown along line 4-4, shown looking towards the top end of the mask with a partial view of the scattering chamber and nasal outgas collector.
Figure 10:
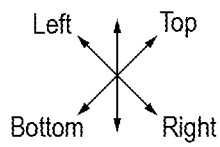

FIG. 10 is a cross-sectional isometric elevation view of the mask of FIG. 6 shown along line 4-4, shown looking towards the top end of the mask with a partial view of the scattering chamber and nasal outgas collector. FIG. 10 shows a mask 100; a shield 102 with a top end 104, a right side 108, a left side 110, an interior surface 112, exterior surface 114, and a wall thickness 116; a skin contacting portion 140; two gas supply inlet ports 130; two gas supply lines 133; two gas supply alignment features 132; a nasal outgas collector 204; two flexible members 210; and two scattering chambers 300, each with a central axis 304, an scattering chamber inlet port 306 with a central axis 314, a flow deflector 308 with a top surface 310, and scattering chamber outlet ports 302. FIG. 10 shows an alternate view of the scattering chamber 300 and its scattering chamber outlet ports 302 as shown in FIGS. 8A and 8B. The various components described in FIG. 10 are merely examples, and other variations, including eliminating components, combining components, and substituting components are all contemplated.

FIG. 11 is a cross-sectional isometric elevation view of the mask of FIG. 6 shown along line 5-5, shown looking towards the top end of the mask with a partial view of the outgas collector channel. FIG. 11 shows a mask 100; a shield 102 with a top end 104, a right side 108, a left side 110, an interior surface 112, an exterior surface 114, and a wall thickness 116; an outgas collector assembly 200 with an oral outgas collector 202, a nasal outgas collector 204, an outgas collector channel 206, and an outgas collector analyzer 208; two gas supply inlet ports 130; two scattering chambers 300, each with a flow detector 308, and scattering chamber outlet ports 302, each with a central axis 312, two flexible members 210; two gas supply lines 133; and two gas supply alignment features 132. FIG. 11 shows an alternate view of the scattering chamber 300 and its scattering chamber outlet ports 302 as shown in FIG. 7. The various components described in FIG. 11 are merely examples, and other variations, including eliminating components, combining components, and substituting components are all contemplated.

Figure 12:
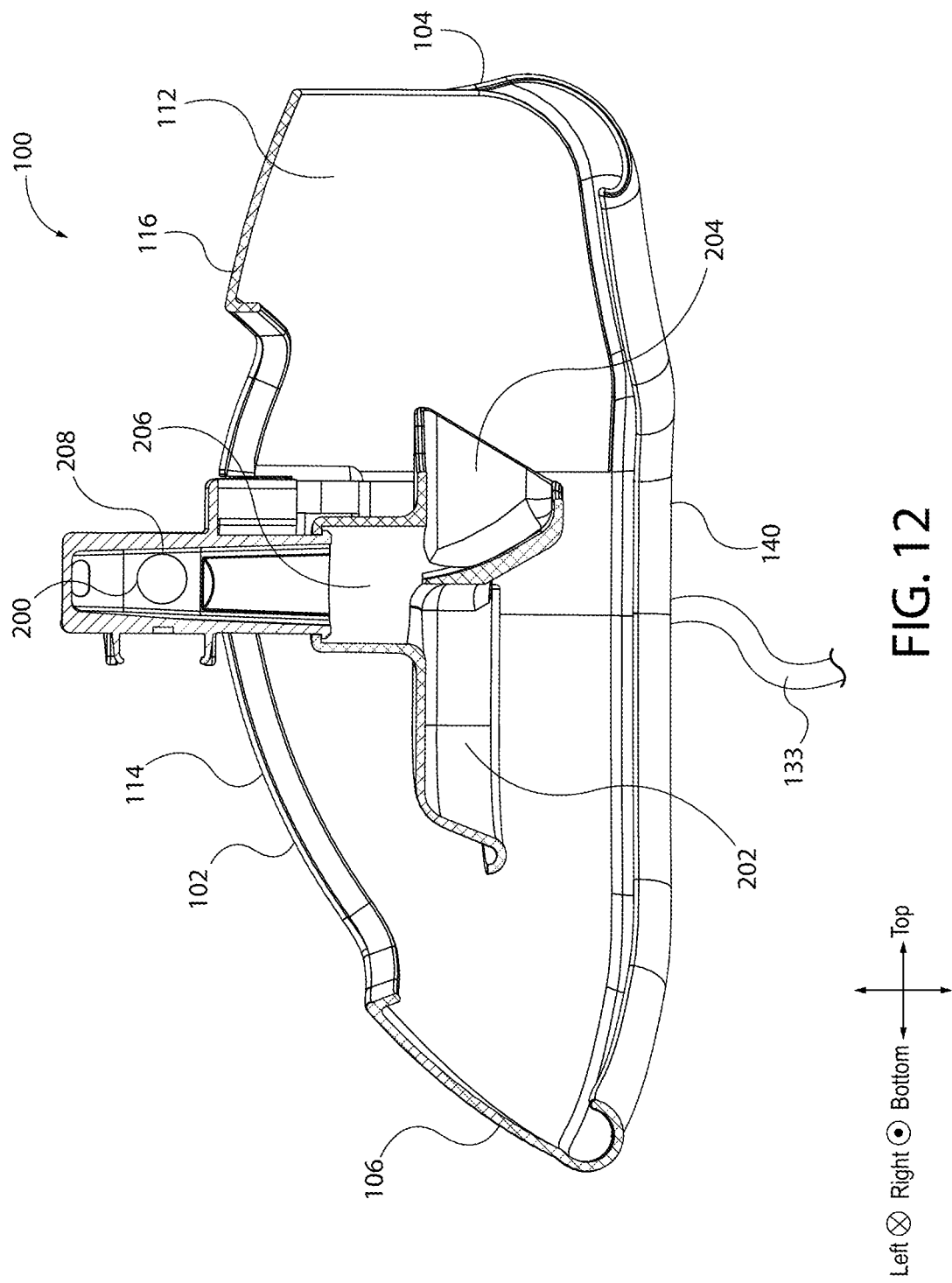
FIG. 12 is a cross-sectional right side elevation view of the mask of FIG. 2 shown along line 6-6, shown looking towards the left side of the mask with a partial view of the oral outgas collector, the nasal outgas collector, and the outgas collector channel.

FIG. 12 is a cross-sectional right side elevation view of the mask of FIG. 2 shown along line 6-6, shown looking towards the left side of the mask with a partial view of the oral outgas collector, the nasal outgas collector, and the outgas collector channel. FIG. 12 shows a mask 100; a shield 102 with a top end 104, a bottom end 106, an interior surface 112, an exterior surface 114, and a wall thickness 116; an outgas collector assembly 200 with an oral outgas collector 202, a nasal outgas collector 204, an outgas collector channel 206, and an outgas collector analyzer 208; and a skin contacting portion 140. FIG. 12 shows an alternate view of the fluid connection between the oral outgas collector 202, the nasal outgas collector 204, and the outgas collector channel 206, as shown in FIG. 3. The various components described in FIG. 12 are merely examples, and other variations, including eliminating components, combining components, and substituting components are all contemplated.

Figure 13:
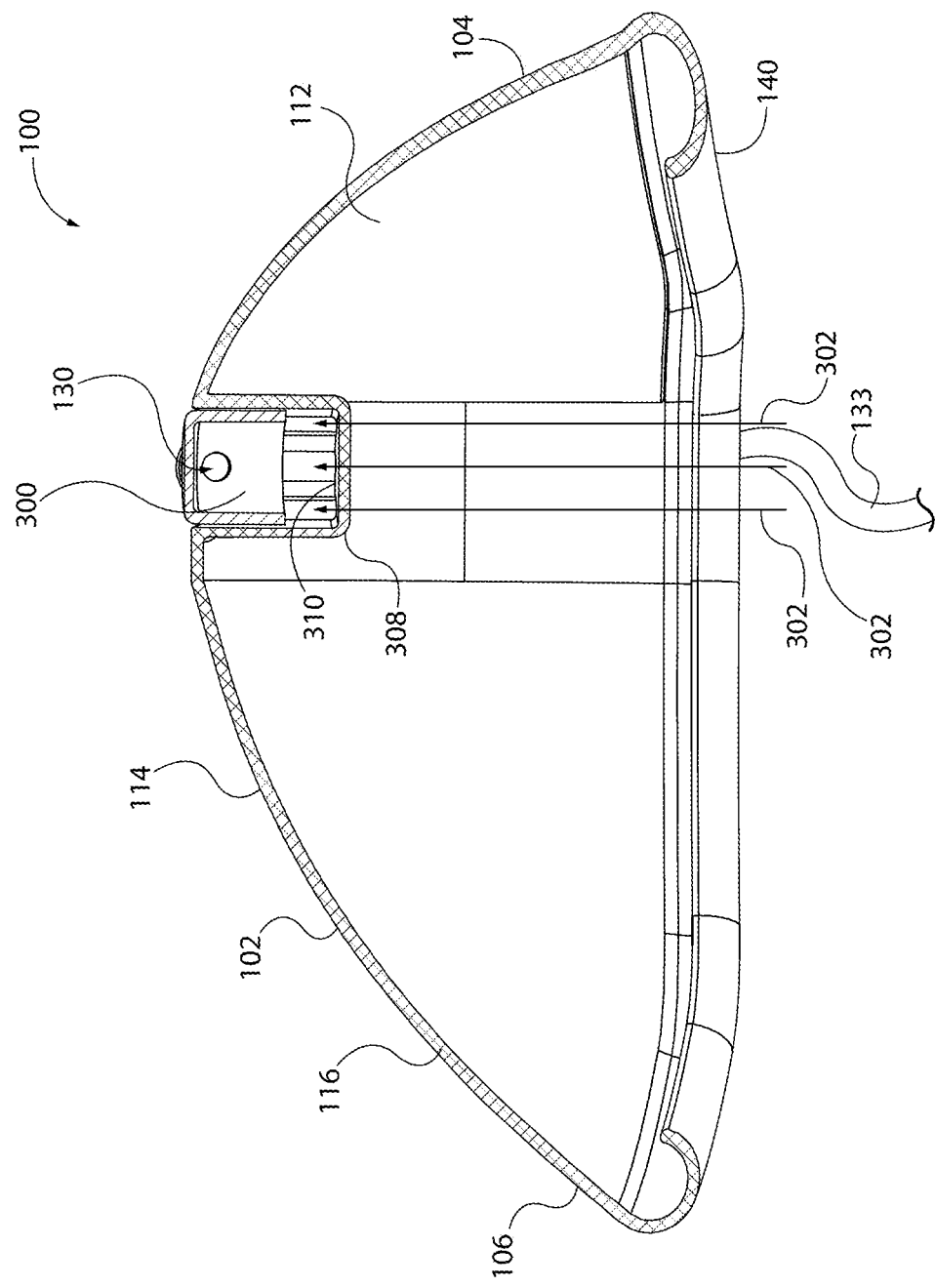
FIG. 13 is a cross-sectional right side elevation view of the mask of FIG. 2 shown along line 7-7, shown looking towards the left side of the mask with a partial view of the scattering chamber.

FIG. 13 is a cross-sectional right side elevation view of the mask of FIG. 2 shown along line 7-7, shown looking towards the left side of the mask with a partial view of the scattering chamber. FIG. 13 shows a mask 100; a shield 102 with a top end 104, a bottom end 106, an interior surface 112, an exterior surface 114, and a wall thickness 116; a gas supply inlet port 130; a scattering chamber 300 with a plurality of scattering chamber outlet ports 302, and a flow deflector 308 with a top surface 310; and a skin contacting portion 140. FIG. 13 shows an alternate view of the scattering chamber 300 and its scattering chamber outlet ports 302 in relation the gas supply inlet port 130. The various components described in FIG. 13 are merely examples, and other variations, including eliminating components, combining components, and substituting components are all contemplated.

Figure 14:
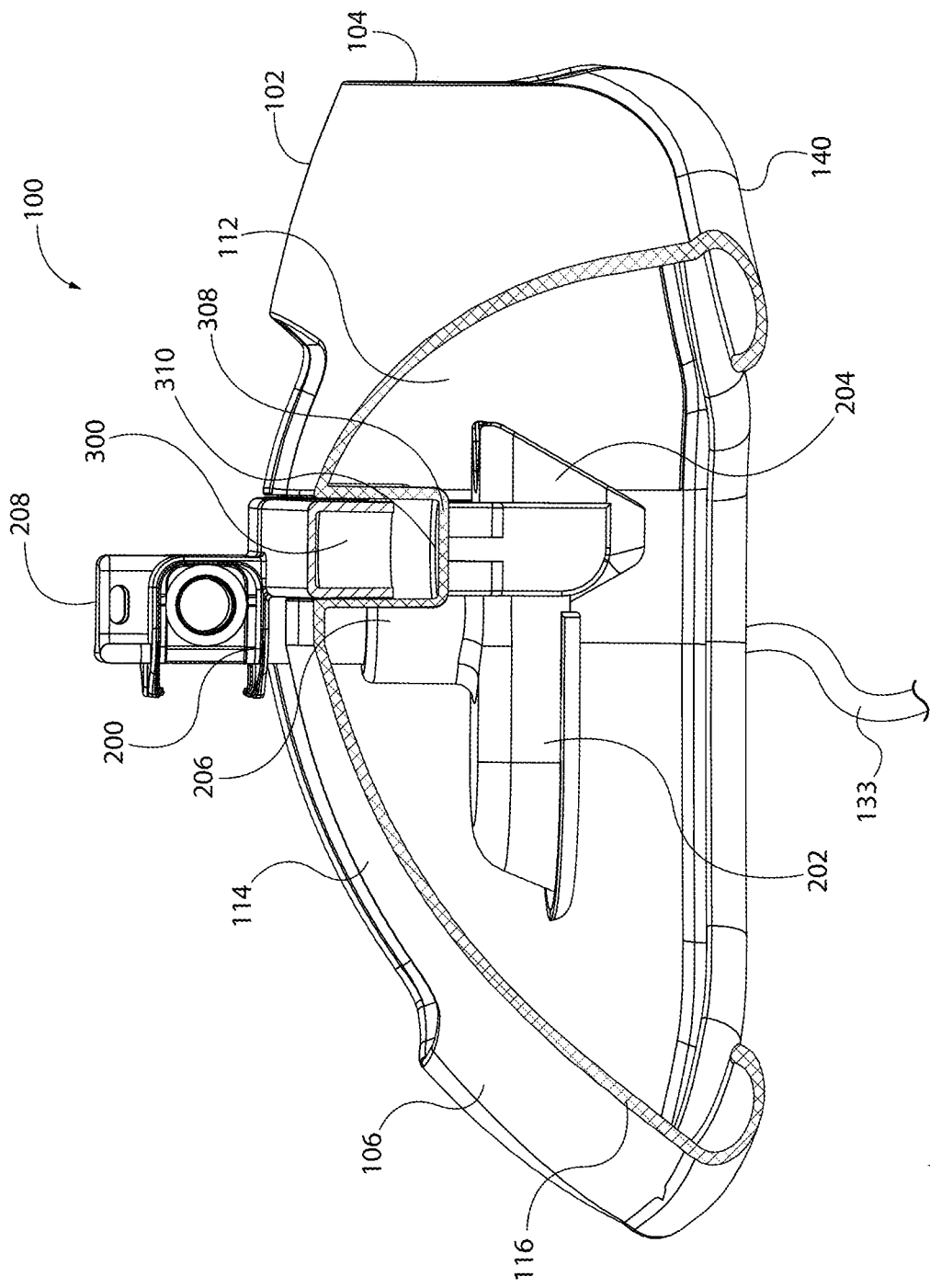
FIG. 14 is a cross-sectional right side elevation view of the mask of FIG. 2 shown along line 8-8, shown looking towards the left side of the mask with a partial view of an alternate scattering chamber.

FIG. 14 is a cross-sectional right side elevation view of the mask of FIG. 2 shown along line 8-8, shown looking towards the left side of the mask with a partial view of an alternate scattering chamber. FIG. 14 shows a mask 100; a shield 102 with a top end 104, a bottom end 106, an interior surface 112, an exterior surface 114, and a wall thickness 116; a scattering chamber 300 with a flow deflector 308 with a top surface 310; an outgas collector assembly 200 with an oral outgas collector 202, a nasal outgas collector 204, an outgas collector channel 206, and an outgas collector analyzer 208; and a skin contacting feature portion 140. FIG. 14 shows an alternate view of the scattering chamber 300 in relation to the outgas collector assembly 200. The various components described in FIG. 14 are merely examples, and other variations, including eliminating components, combining components, and substituting components are all contemplated.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. A mask configured to assist the respiration of a patient, the mask comprising:
   a gas inlet port positioned to connect a gas supply to the mask and direct gas flow towards a patient's skin;
   a scattering chamber with a scattering chamber inlet port and a plurality of scattering chamber outlet ports, the scattering chamber inlet port fluidly connected to the gas inlet port, and the plurality of scattering chamber outlet ports positioned such that the gas flowing through the plurality scattering chamber outlet ports is directed away from the patient's skin and towards the interior surface of the mask and a region between the patient's skin and the interior surface of the mask;
   wherein the scattering chamber further comprises a flow deflector configured to direct the gas supply flow from the scattering chamber inlet port to the scattering chamber outlet ports; and an outgas collector assembly positioned adjacent to at least one of the patient's oral or nasal passage and configured to collect an outgas emission expelled from the patient, wherein the outgas collector assembly is connected adjacent the scattering chamber and eject the outgas emission from the mask.

2. The mask of claim 1, wherein a central axis of the scattering chamber inlet port is substantially perpendicular to a central axis of the scattering chamber.

3. The mask of claim 2, wherein the scattering chamber outlet ports are located in a lower portion of the scattering chamber and each scattering chamber outlet port has a central axis substantially parallel to the top surface of the flow deflector.

4. The mask of claim 3, wherein the scattering chamber outlet ports are rectangular, circular, or elliptical apertures, or combinations thereof.

5. The mask of claim 1, wherein the scattering chamber further comprises an adjustable member to allow for the adjustment of the flow of the gas supply through the scattering chamber.

6. The mask of claim 5, wherein the adjustable member is rotatably adjacent to at least one scattering chamber outlet port.

7. The mask of claim 5, wherein the adjustable member is slidably adjacent to at least one scattering chamber outlet port.

8. The mask of claim 1, wherein the outgas collector assembly comprises an oral outgas collector and at least one nasal outgas collector.

9. The mask of claim 8, wherein an air gap is defined between the patient and the oral outgas collector when the mask is in normal use.

10. The mask of claim 8, wherein the outgas collector assembly further comprises an outgas composition analyzer fluidly connected to the oral outgas collector and the at least one nasal outgas collector.

11. The mask of claim 8, wherein the nasal outgas collector is flexibly connected to the mask.

12. The mask of claim 1, wherein the interior surface of the mask is positioned to reflect the scattered gas supply flow back towards to a patient's oral and nasal passage for inhalation of the gas by the patient.

13. The mask of claim 12, wherein a sensor fluidly is connected to the region between the patient's skin and the interior surface of the mask.

14. The mask of claim 1, wherein a cross-sectional area of the plurality of output ports is selected, based at least in part, on a desired volumetric flow rate.

15. The mask of claim 1, wherein a portion of the outgas collector assembly is removable.

16. A method of protecting a patient's skin during supplemental respiration using a mask, the method comprising;

introducing gas to a gas supply inlet port of the mask, wherein the gas supply inlet port is positioned to direct the gas towards a patient's face;

diverting the gas away from the patient's face by flowing the gas through a plurality of scattering chamber outlet ports of a scattering chamber of the mask; whereby directing the gas through a scattering chamber inlet towards a flow deflector; deflecting the flowing gas supply off of the flow deflector; and directing the deflected flowing gas supply to flow out of at least one scattering chamber outlet port; and collecting, when the patient exhales, the patient's outgas in an outgas collector assembly positioned adjacent to at least one of the patient's oral or nasal passage.

17. The method of claim 16, further comprising collecting a patient's outgas in an outgas collector assembly that is spaced apart from the patient's skin.

18. The method of claim 17, further comprising analyzing a composition of the patient's outgas.

19. The method of claim 16, where the scattering chamber comprises a scattering chamber inlet port with a central axis that is parallel to a central axis of at least one scattering chamber outlet port.

20. The method of claim 16, wherein the at least one scattering chamber outlet port is a circular, rectangular or elliptical aperture, or combinations thereof.

21. The method of claim 16, further comprising calculating a cross-sectional area of the at least one scattering chamber outlet port;

calculating a volumetric flow rate of the flowing gas supply through the scattering chamber based upon the calculated cross-sectional area of the at least one scattering chamber outlet port.

22. The method of claim 16, further comprising adjusting a cross-sectional area of the at least one scattering chamber outlet port by rotating a first portion of the scattering chamber about a second portion of the scattering chamber to select a desired flow rate of the gas through the scattering chamber outlet.

23. The method of claim 16, further comprising adjusting a cross-sectional area of the at least one scattering chamber outlet port by sliding a first portion of the scattering chamber adjacent a second portion of the scattering chamber to vary the flow of the supplied gas flowing through the at least one scattering chamber outlet port.

24. The method of claim 16, further comprising analyzing a composition of the diverted gas contacting the interior surface of the mask.

* * * * *